(12) United States Patent
Copp-Howland et al.

(10) Patent No.: US 8,942,830 B2
(45) Date of Patent: Jan. 27, 2015

(54) ELECTRODE DELIVERY SYSTEM

(71) Applicant: Covidien LP, Mansfield, MA (US)

(72) Inventors: Warren Copp-Howland, Chicopee, MA (US); Erick Garstka, Westfield, MA (US); David Selvitelli, Suffield, CT (US); Kathleen Tremblay, Westfield, MA (US); Caroline Gasiorski, Feeding Hills, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/850,323

(22) Filed: Mar. 26, 2013

(65) Prior Publication Data

US 2013/0289689 A1 Oct. 31, 2013

Related U.S. Application Data

(63) Continuation of application No. 12/886,926, filed on Sep. 21, 2010, now Pat. No. 8,428,751.

(60) Provisional application No. 61/315,159, filed on Mar. 18, 2010.

(51) Int. Cl.
*A61N 1/04* (2006.01)
*A61N 1/39* (2006.01)
*A61B 19/02* (2006.01)

(52) U.S. Cl.
CPC .............. *A61N 1/046* (2013.01); *A61N 1/3925* (2013.01); *A61N 1/3993* (2013.01); *A61N 1/3968* (2013.01); *A61B 2562/125* (2013.01); *A61B 19/026* (2013.01)
USPC ........................................................ 607/142

(58) Field of Classification Search
None
See application file for complete search history.

(56) References Cited

U.S. PATENT DOCUMENTS

| 4,779,630 A | 10/1988 | Scharnberg et al. |
| 5,462,157 A | 10/1995 | Freeman et al. |
| 5,645,527 A | 7/1997 | Beck |
| 5,797,867 A | 8/1998 | Guerrera et al. |

(Continued)

FOREIGN PATENT DOCUMENTS

| JP | 2004-520153 | 7/2004 |
| JP | 2006-516208 | 6/2006 |

(Continued)

OTHER PUBLICATIONS

Notice of Allowance; dated Jan. 2, 2013; for U.S. Appl. No. 12/886,926; filed Sep. 21, 2010; issued as U.S. Pat. No. 8,428,751; issued on Apr. 23, 2013; 5 pages.

(Continued)

*Primary Examiner* — Brian T Gedeon
(74) *Attorney, Agent, or Firm* — Lisa E. Winsor, Esq.

(57) ABSTRACT

An automatic external defibrillator configured to deliver electrical pulses and/or shocks to a heart of a patient during a cardiac emergency includes a housing supporting an electrical connector; a defibrillator electrode delivery system supported on the housing and a pair of defibrillation electrode pads supported by the defibrillator electrode delivery system. Each of the pair of defibrillation electrode pads is pre-connected to the electrical connector of the housing. A hydrogel layer of each defibrillation electrode pad is retained by the defibrillator electrode delivery system in such a manner so as to reduce a moisture vapor transmission rate thereof.

12 Claims, 3 Drawing Sheets

(56) References Cited

U.S. PATENT DOCUMENTS

| | | |
|---|---|---|
| 5,797,969 A | 8/1998 | Olson et al. |
| 5,817,151 A | 10/1998 | Olson et al. |
| 6,083,246 A | 7/2000 | Stendahl et al. |
| 6,115,638 A | 9/2000 | Groenke |
| 6,314,320 B1 | 11/2001 | Powers et al. |
| 6,321,113 B1 | 11/2001 | Parker et al. |
| 6,556,864 B1 | 4/2003 | Picardo et al. |
| 6,662,046 B2 | 12/2003 | Hansen |
| 6,662,056 B2 | 12/2003 | Picardo et al. |
| 6,675,051 B2 | 1/2004 | Janae et al. |
| 6,872,080 B2 | 3/2005 | Pastrick et al. |
| 6,874,621 B2 | 4/2005 | Solosko et al. |
| 6,928,322 B2 | 8/2005 | Yerkovich et al. |
| 6,948,295 B2 | 9/2005 | Biggins |
| 6,965,799 B2 | 11/2005 | Nova et al. |
| 6,969,259 B2 | 11/2005 | Pastrick et al. |
| 7,069,074 B2 | 6/2006 | Covey et al. |
| 7,072,712 B2 | 7/2006 | Kroll et al. |
| 7,231,247 B2 | 6/2007 | Faller et al. |
| 7,236,823 B2 | 6/2007 | Herbert |
| RE40,365 E | 6/2008 | Kirchgeorg et al. |
| 7,453,354 B2 | 11/2008 | Reiter et al. |
| 7,457,662 B2 | 11/2008 | Nassif |
| 7,463,923 B2 | 12/2008 | Brewer et al. |
| 7,489,972 B2 | 2/2009 | Denney et al. |
| 7,792,577 B2 | 9/2010 | Hamilton et al. |
| 7,797,044 B2 | 9/2010 | Covey et al. |
| 8,428,751 B2 | 4/2013 | Copp-Howland et al. |
| 2006/0058846 A1 | 3/2006 | Smirles et al. |
| 2007/0235555 A1 | 10/2007 | Helf et al. |
| 2007/0255382 A1 | 11/2007 | Meyer et al. |
| 2009/0227857 A1 | 9/2009 | Rowe et al. |
| 2009/0270709 A1 | 10/2009 | Copp et al. |
| 2009/0270710 A1 | 10/2009 | Copp et al. |
| 2009/0281585 A1 | 11/2009 | Katzman et al. |
| 2010/0072060 A1 | 3/2010 | Copp-Howland |
| 2011/0230925 A1 | 9/2011 | Copp-Howland et al. |

FOREIGN PATENT DOCUMENTS

| | | |
|---|---|---|
| JP | 2006-517692 | 5/2008 |
| WO | WO 02/098192 | 12/2002 |
| WO | WO 2004/064919 | 8/2004 |
| WO | WO 2006/046160 | 5/2006 |
| WO | WO 2007/084442 A2 | 7/2007 |
| WO | WO 2007/127266 | 11/2007 |

OTHER PUBLICATIONS

Response to Office Action dated Feb. 12, 2014, for U.S. Appl. No. 13/628,063, 8 pages.
Non-Final Office Action dated Oct. 11, 2013 for U.S. Appl. No. 13/628,063.
Response filed on Jan. 10, 2014 to Non-Final Office dated Oct. 11, 2013 for U.S. Appl. No. 13/628,063.
Final Office Action dated Feb. 12, 2014 for U.S. Appl. No. 13/628,063.
"Lifesaving Products;" Laerdal Products Catalogue 2008-2009; Jan. 2008; 148 pages.
Office Action dated Aug. 15, 2012; for U.S. Appl. No. 12/886,926; 15 pages.
Response filed Nov. 14, 2012; to Office Action dated Aug. 15, 2012; for U.S. Appl. No. 12/886,926; 14 pages.
Notice of Allowance; dated Jan. 2, 2013; for U.S. Appl. No. 12/886,926, filed on Sep. 21, 2010; issued as U.S. Pat. No. 8,428,751; issued on Apr. 23, 2013; 5 pages.
European Search Report; dated Jun. 8, 2011; for EP Pat. App. No. 11157002.4; 6 pages.
Office Action dated Jul. 8, 2014 from U.S. Appl. No. 13/628,063.
Japanese Office Action (with English Translation) with mailing dated on Jul. 16, 2014 corresponding to JP Pat. Appl. No. 2011-059943, 7 pages.

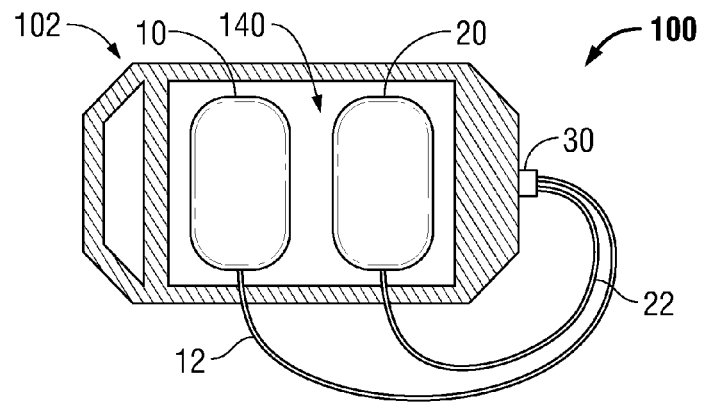
FIG. 1
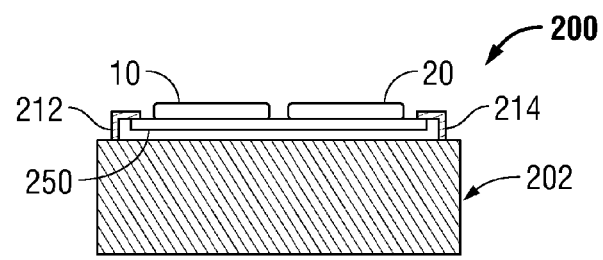
FIG. 2
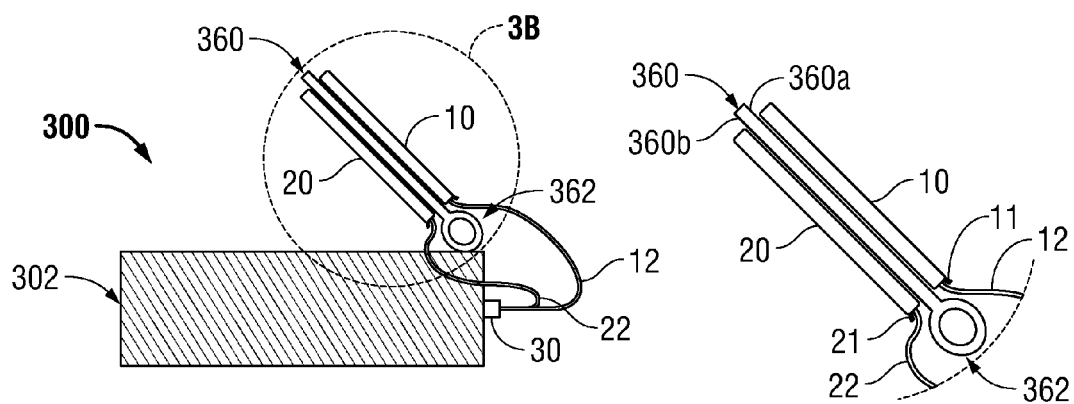
FIG. 3A  FIG. 3B

ELECTRODE DELIVERY SYSTEM

CROSS-REFERENCE TO RELATED APPLICATIONS

The present application is a continuation of U.S. patent application Ser. No. 12/886,926 filed on Sep. 21, 2010 by Warren et al., which claims the benefit of and priority to U.S. Provisional Application Ser. No. 61/315,159, filed on Mar. 18, 2010, entitled "Electrode Delivery System," the entire contents of each application being incorporated herein by reference.

BACKGROUND

1. Technical Description

The present disclosure relates to defibrillator and defibrillation electrodes and, more particularly, to systems, methods and packages to facilitate the use and connection of defibrillation electrodes to a defibrillator prior to the electrodes being used on a patient, while allowing the electrodes to maintain a sufficient amount of moisture to be able to properly function.

2. Background of Related Art

Electrodes which are typically used in medical applications generally include a conductor and a connector. The connector is attached at one end to the conductor and includes a plug at the other end to be plugged into a defibrillator or other device. The conductor is often covered or coated in a conductive gel, which enhances its ability to adhere to a patient's skin. When the conductive gel becomes too dry, it may lose its ability to adhere to a patient or demonstrate excessively high contact impedance. To prevent the conductive gel from drying out, the electrode may be stored in a package prior to use.

In a medical setting, there are often a variety of different defibrillators and electrodes at a clinician's disposal and it is not uncommon for several of the defibrillators and electrodes to have different manufacturers. Compatibility among defibrillators (or other medical devices) and electrodes of different brands is often lacking, which can cause confusion as to which particular electrode to use with a given defibrillator. Thus, clinicians open electrode packages to determine if the electrode (or electrode plug) is compatible with the defibrillator. If the electrode (or electrode plug) is not compatible with the defibrillator, the opened electrode is set aside and the clinician would open a different packaged electrode. As can be appreciated, testing electrodes in this fashion leads to waste, as the electrodes that are not compatible are likely to become too dry if not used in a timely fashion.

Further, in preparation for an emergency situation, clinicians may perform as many steps as possible before such an emergency situation arises. For example, a clinician may prepare a defibrillator by "pre-connecting" a compatible electrode to the defibrillator. Pre-connecting a compatible electrode to a defibrillator prevents rapid diffusion of moisture from the conductive gel, and reduces the number of steps that are needed to take place during an actual emergency.

In many instances, when an emergency situation arises at a public location remote from a medical facility, Automatic External Defibrillators (AED's) may generally be available for use on the individual experiencing the medical emergency. An AED is a portable electronic device that automatically diagnoses the potentially life threatening cardiac arrhythmias of ventricular fibrillation and ventricular tachycardia in a patient, and is able to treat them through defibrillation, the application of electrical therapy which stops the arrhythmia, allowing the heart to reestablish an effective rhythm.

A need exists for a system of delivering electrodes to a patient that is easier to use and more simple to use, and that reduces the time required for a user of the AED to set-up the AED.

SUMMARY

The present disclosure relates to systems, methods and packages to facilitate the use and connection of defibrillation electrodes to a defibrillator prior to the electrodes being used on a patient, while allowing the electrodes to maintain a sufficient amount of moisture to be able to properly function. According to an aspect of the present disclosure, an automatic external defibrillator includes a defibrillator housing having circuitry adapted to deliver electrical signals to a heart of a subject during a cardiac emergency, and with at least one electrode support surface associated therewith, and a pair of defibrillation electrode pads in electrical communication with the circuitry of the defibrillator housing. The electrode pads each have a conductive hydrogel layer, which is mounted to the at least one electrode support surface of the defibrillator housing when in a stored condition thereof with the hydrogel layer in releasable secured contacting relation with the at least one electrode support surface. With this relationship, moisture loss of the hydrogel layer is substantially minimized when the electrode pads are in the stored condition to thereby sustain operability of the electrode pads until when the electrode pads are detached from the electrode support surface to assume an operable condition for application to the subject.

The at least one electrode support surface may be an outer surface of the defibrillator housing. The at least one electrode support surface may include a coating dimensioned and adapted to facilitate release of each electrode pad from the at least one electrode support surface to assume the operable condition.

A carrier member may be mounted to the defibrillator housing. The carrier member has opposed sides defining opposed electrode support surfaces with the electrode pads being mounted to respective opposed sides of the carrier member. The carrier member may be mounted to the defibrillator housing via a hinge. The electrode pads each may include a pull tab to facilitate removal of the electrode pads from the respective opposed sides of the carrier member.

In another embodiment, an automatic external defibrillator includes a defibrillator housing having circuitry adapted to deliver electrical signals to a heart of a subject during a cardiac emergency and an electrical connector, a pair of defibrillation electrode pads pre-connected to the electrical connector of the housing with each electrode pad having a conductive hydrogel layer and a pair of spaced apart brackets extending from the housing. The brackets may be configured and dimensioned to operatively engage the electrode pads to retain the electrode pads in fixed relation to the housing when in a stored condition thereof and permit release of the electrode pads to an operable condition for application to the subject. The electrode pads may have a release liner adhered to the hydrogel layer to minimize moisture loss when in the stored condition. The release liner may be sized to extend across a space defined by the pair of brackets with the brackets being configured to retain the release liner in close proximity to the housing.

In accordance with another aspect of the disclosure, an automatic external defibrillator includes a defibrillator housing having circuitry adapted to deliver electrical signals to a heart of a subject during a cardiac emergency and a pair of defibrillation electrode pads in electrical communication with the circuitry of the defibrillator housing. The electrode pads each have a conductive hydrogel layer, and at least one release liner is releasably adhered to the conductive hydrogel layer to minimize moisture loss of the hydrogel layer. A two-part fastener mechanism selectively secures each of the pair of defibrillation electrode pads to the housing. At least one first member of the two-part fastener mechanism is secured to the housing and at least one second member of the two-part fastener mechanism is secured to the electrode pads. The electrode pads may include at least one backing member. The at least one backing member has the at least one second member of the two-part fastener mechanism mounted thereto. The two-part fastener mechanism may include a hook and loop fastener system.

In another aspect of the disclosure, an automatic external defibrillator configured to deliver electrical pulses and/or shocks to a heart of a patient during a cardiac emergency includes a housing having circuitry with a battery adapted to deliver electrical signals to a heart of a subject during a cardiac emergency, a pair of contact pads disposed on a surface of the housing and a pair of defibrillation electrode pads in electrical communication with the circuitry. Each electrode pad is releasably mounted to a respective contact pad when in a stored condition thereof. The circuitry is automatically activated by a separation of at least one of the pair of defibrillation electrode pads from the respective contact pad.

BRIEF DESCRIPTION OF THE DRAWINGS

Various embodiments of electrode delivery systems are described herein with reference to the drawings wherein:

FIG. 1 is a top, plan view of a defibrillator electrode delivery system according to an embodiment of the present disclosure;

FIG. 2 is a side, elevational view of a defibrillator electrode delivery system according to another embodiment of the present disclosure;

FIG. 3A is a side, elevational view of a defibrillator electrode delivery system according to a further embodiment of the present disclosure;

FIG. 3B is an enlarged view of the indicated area of detail of FIG. 3A;

DETAILED DESCRIPTION

Figure 4:
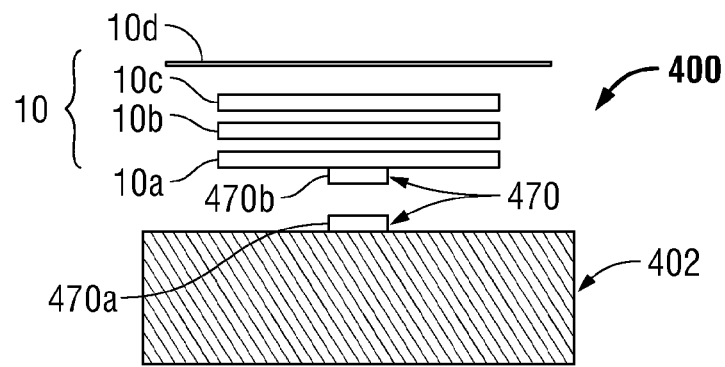
FIG. 4 is a side, elevational view, with parts separated, of a defibrillator electrode delivery system according to yet another embodiment of the present disclosure.

Embodiments of the presently disclosed defibrillator electrode delivery system will now be described in detail with reference to the drawing figures wherein like reference numerals identify similar or identical elements.

As illustrated in FIG. 1, a defibrillator electrode delivery system, according to an embodiment of the present disclosure, is generally designated as 100. Defibrillator electrode delivery system 100 includes an automatic external defibrillator (AED) 102 defining a surface 140 configured to store or retain a pair of electrode pads 10, 20. Electrode pads 10, 20 are electrically connectable to or pre-connected to AED 102 via respective lead wires 12, 22 joined at a connector 30.

Surface 140 is coated with a release material to selectively adhere electrode pads 10, 20 thereto and to facilitate the removal of electrode pads 10, 20 therefrom when needed. For example, the release material may be Teflon, silicone, and combinations thereof.

In this configuration, a gel layer of each electrode pad 10, 20 has a reduced tendency to dry-out. Due to the adherence of the electrode pads 10, 20 to surface 140 of AED 102, no special packaging is required that reduces a moisture vapor transmission rate (MVTR) of the electrode pads 10, 20.

As illustrated in FIG. 2, a defibrillator electrode delivery system, according to another embodiment of the present disclosure, is generally designated as 200. Defibrillator electrode delivery system 200 includes an automatic external defibrillator (AED) 202 having a pair of spaced apart brackets 212, 214 supported on a surface thereof. Defibrillator electrode delivery system 200 is configured to store or retain a pair of electrode pads 10, 20 that are supported on a release liner 250. Brackets 212, 214 are spaced apart an amount sufficient to engage, capture and/or lock down on release liner 250 to thereby maintain electrode pads 10, 20 secured to AED 202. Electrode pads 10, 20 are electrically connected to AED 202 via respective lead wires (not shown) joined at a connector (not shown).

In this configuration, a gel layer of each electrode pad 10, 20 has a reduced tendency to dry-out. Due to the adherence of the electrode pads 10, 20 to release liner 250, no special packaging is required that reduces a moisture vapor transmission rate (MVTR) of the electrode pads 10, 20.

As illustrated in FIGS. 3A and 3B, a defibrillator electrode delivery system, according to a further embodiment of the present disclosure, is generally designated as 300. Defibrillator electrode delivery system 300 includes an automatic external defibrillator (AED) 302 having a carrier flap or page 360 hingedly connected thereto via a hinge member 362. Defibrillator electrode delivery system 300 is configured to store or retain a pair of electrode pads 10, 20 that are supported on a front side, a back side and/or on opposed sides 360a, 360b of flap 360 (as shown in FIGS. 3A and 3B). As shown in FIG. 3B, each electrode pad 10, 20 may include a respective pull tab 11, 21 to facilitate the removal of electrode pads 10, 20 from flap 360. Electrode pads 10, 20 are electrically connectable to or pre-connected to AED 302 via respective lead wires 12, 22 joined at a connector 30.

In this configuration, a gel layer of each electrode pad 10, 20 has a reduced tendency to dry-out. Due to the adherence of the electrode pads 10, 20 to flap 360, no special packaging is required that reduces a moisture vapor transmission rate (MVTR) of the electrode pads 10, 20.

As illustrated in FIG. 4, a defibrillator electrode delivery system, according to still another embodiment of the present disclosure, is generally designated as 400. Defibrillator electrode delivery system 400 includes an automatic external defibrillator (AED) 402 having a two-part fastener member 470 associated therewith for selectively securing a pair of electrode pads thereto (only one electrode pad 10 being shown). Two-part fastener member 470 includes a first part 470a secured to AED 402 and a second part 470b secured to a backing layer 10a of electrode pad 10. Electrode 10 includes a conductive and/or non-conductive substrate 10b overlying backing layer 10a, on a side opposite the second part 470b of the two-part fastener member 470. Electrode 10 further includes a gel or hydrogel layer 10c overlying substrate 10b, and a liner 10d overlying gel or hydrogel layer 10c.

Two-part fastener member 470 may be in the form of a hook and loop type fastener where one of the first part 470a and the second part 470b is the hook portion and the other of the first part 470a and the second part 470b is the loop portion. It is contemplated that the two-part fastener member 470 may include double-sided tape or the like.

In this configuration, a gel or hydrogel layer 10e of electrode pad 10 has a reduced tendency to dry-out. Due to the securement of the electrode pad 10 to AED 402 and to the provision of a liner 10d overlying gel or hydrogel layer 10c, no special packaging is required that reduces a moisture vapor transmission rate (MVTR) of the electrode pads.

Figure 5:
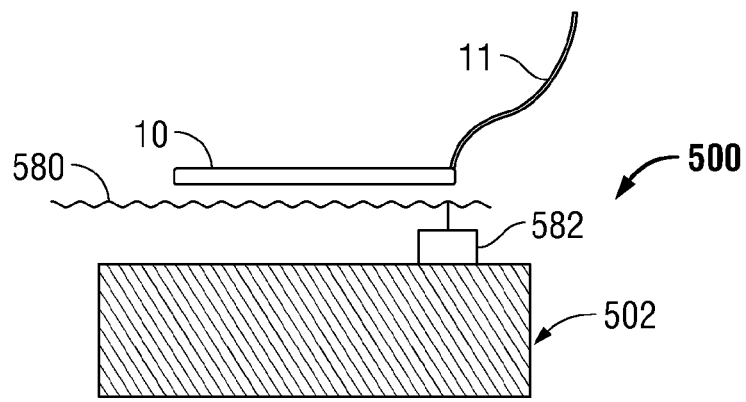
FIG. 5 is a side, elevational view of a defibrillator electrode delivery system according to still another embodiment of the present disclosure.

As illustrated in FIG. 5, a defibrillator electrode delivery system, according to another embodiment of the present disclosure, is generally designated as 500. Defibrillator electrode delivery system 500 includes an automatic external defibrillator (AED) 502 having a release liner 580 secured to a surface thereof via a clamp 582. Defibrillator electrode delivery system 500 is configured to store or retain at least one electrode pad 10 on a front side 580a of release liner 580. As shown in FIG. 5, electrode pad 10 may include a pull tab 11 to facilitate the removal of electrode pad 10 from release liner 580.

In this configuration, a gel layer of electrode pad 10 has a reduced tendency to dry-out. Due to the adherence of the electrode pad 10 to release liner 580, no special packaging is required that reduces a moisture vapor transmission rate (MVTR) of the electrode pads 10, 20.

Figure 6:
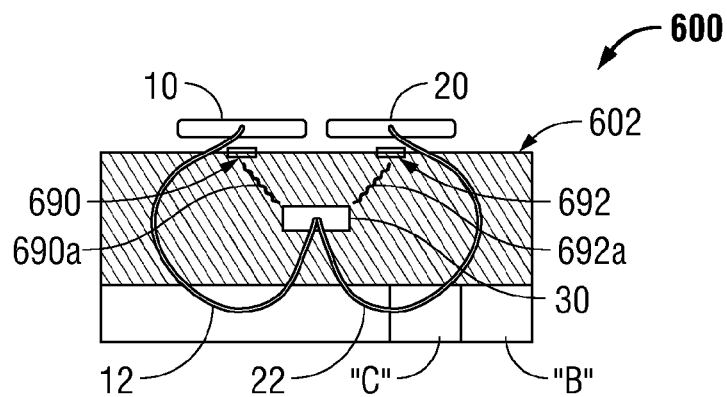
FIG. 6 is a side, elevational view of a defibrillator electrode delivery system according to another embodiment of the present disclosure.

As illustrated in FIG. 6, a defibrillator electrode delivery system, according to yet another embodiment of the present disclosure, is generally designated as 600. Defibrillator electrode delivery system 600 includes an automatic external defibrillator (AED) 602 including a pair of electrical contact points or pads 690, 692 disposed in a surface thereof. Defibrillator electrode delivery system 600 includes a pair of electrode pads 10, 20 electrically connectable to or pre-connected to AED 602 via respective lead wires 12, 22 joined at a connector 30. Electrode pads 10, 20 are also in contact with respective contact pads 690, 692. Each electrical contact pad 690, 692 is electrically connected to a respective electrical connector 690a, 692a which electrically interconnected to respective lead wires 12, 22 by way of connector 30.

In this manner, a first electrical circuit is defined which includes contact pad 690, a respective electrical connector 690a, connector 30, lead wire 12 and electrode pad 10. Also, a second electrical circuit is defined which includes contact pad 692, a respective electrical connector 692a, connector 30, lead wire 22 and electrode pad 20.

AED 602, as schematically shown in FIG. 6, includes a battery "B" and high voltage circuitry "C" disposed in a housing 602a thereof. The battery and the high voltage circuitry are electrically connected to connector 30 and/or electrical connectors 690a, 690b.

It is contemplated that as electrode pads 10, 20 are lifted or separated from AED 602, that electrode pads 10, 20 separate from contact pads 690, 692, altering an impedance or breaking a respective circuit therebetween, and thereby causing AED 602 to automatically begin to power-up or initialize (i.e., run an automated set-up process with readies AED 602 prior to use in a cardiac emergency). It is further contemplated that AED 602 is automatically powered-up upon a separation of any one of electrode pads 10, 20 from contact pads 690, 692 of AED 602.

Alternatively, or in addition to the automated set-up process, as so configured, an impedance check may be performed across each electrode pad 10, 20 to check an impedance of each electrode pad 10, 20 and determine if a moisture content of a gel layer of each electrode pad 10, 20 is acceptable for use thereof.

Figure 7:
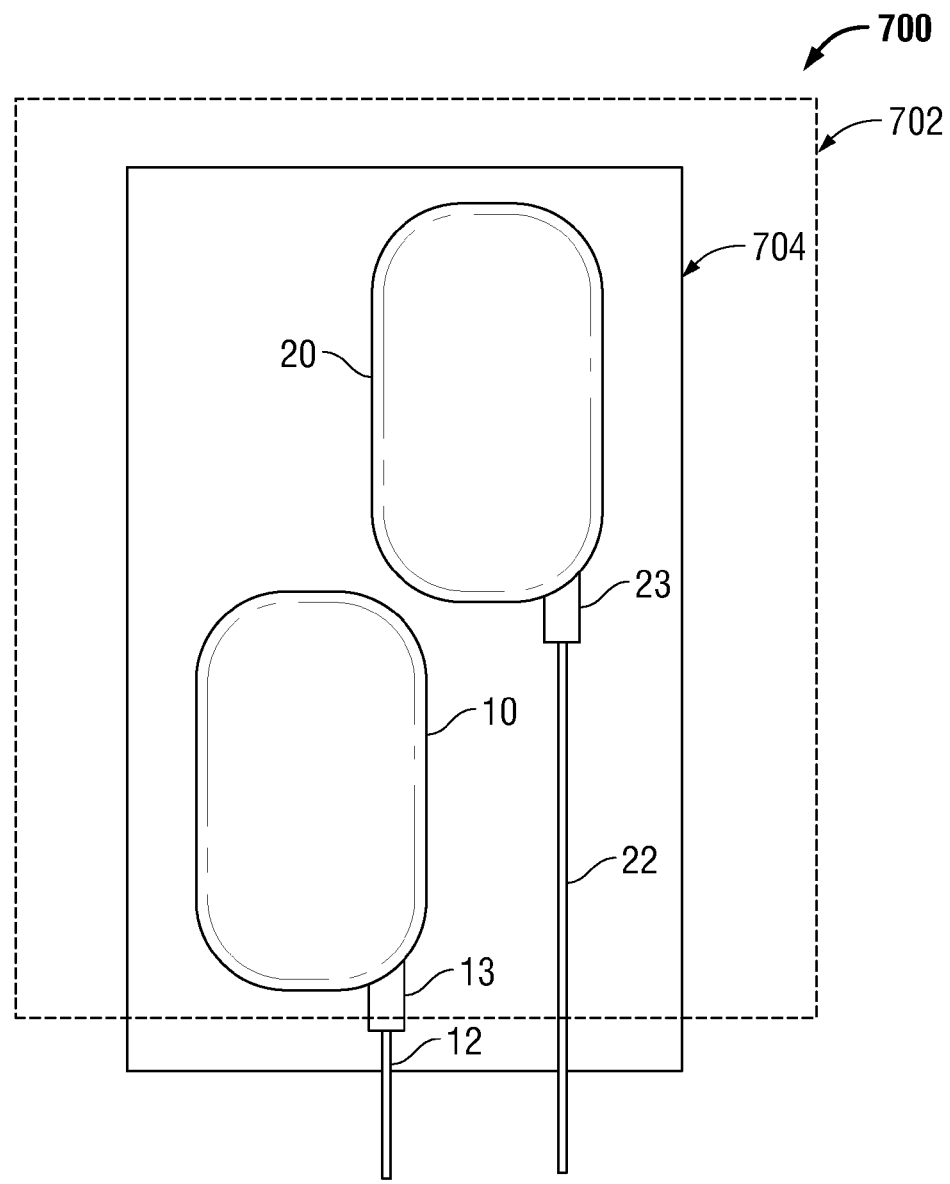
FIG. 7 is a top, plan view of a defibrillator electrode delivery system according to another embodiment of the present disclosure.

As illustrated in FIG. 7, a defibrillator electrode delivery system, according to still another embodiment of the present disclosure, is generally designated as 700. Defibrillator electrode delivery system 700 includes an automatic external defibrillator (AED) 702 including a pair of electrode pads, an apex electrode pad 10 and a sternum electrode pad 20. Electrode pads 10, 20 are electrically connectable to or pre-connected to AED 702 via respective lead wires 12, 22. Apex electrode pad 10 includes a pull tab 13 that projects from or extends from a perimeter of a box or liner 704 disposed on AED 702, which retains electrode pads 10, 20. Electrode pads 10, 20 are arranged on box or liner 704 such that, as apex electrode pad 10 is peeled off of box or liner 704, liner 704 rolls forward and exposes a pull tab 23 of sternum electrode pad 20 so that the sternum electrode pad 20 is ready to be removed from liner 704 after placement of apex electrode pad 10 is placed against the patient.

In accordance with any of the embodiments of the present disclosure described above, it is contemplated that as electrode pads 10, 20 are removed from or separated from the surface of the AED, that the AED may automatically begin to power-up.

Electrode pads configured for use with any of the electrode delivery systems disclosed herein are shown and described in International Patent Application Serial No. PCT/US2007/010060, filed Apr. 27, 2007, in U.S. patent application Ser. No. 12/237,803, filed on Sep. 25, 2008, and U.S. Patent Application Publication No. 2009/0227857, filed on Mar. 6, 2008, the entire content of each of which being incorporated herein by reference.

An example of a suitable polymer which may be utilized in the electrode pads disclosed herein includes RG-63B hydrogel, commercially available from Tyco Healthcare Group d/b/a/Covidien. Other suitable hydrogels include those disclosed in U.S. Patent Application Publication No. 2009/0270709, filed on Oct. 30, 2009, and U.S. Patent Application Publication No. 2009/0270710, filed on Oct. 30, 2009, the entire disclosures of each of which are incorporated by reference herein for all purposed.

It is to be understood that the foregoing description is merely a disclosure of particular embodiments and is in no way intended to limit the scope of the disclosure. Other possible modifications will be apparent to those skilled in the art and are intended to be within the scope of the present disclosure.

What is claimed is:

1. An automatic external defibrillator, which comprises:
    a defibrillator housing including circuitry adapted to deliver electrical signals to a heart of a subject during a cardiac emergency, the defibrillator housing having at least one electrode support surface associated therewith; and
    a pair of defibrillation electrode pads in electrical communication with the circuitry of the defibrillator housing, the electrode pads each having a conductive hydrogel layer, and being mounted to the at least one electrode support surface of the defibrillator housing when in a stored condition thereof with the hydrogel layer in releasable secured contacting relation with the at least one electrode support surface, whereby moisture loss of the hydrogel layer is substantially minimized when the electrode pads are in the stored condition to thereby sustain operability of the electrode pads until when the electrode pads are detached from the electrode support surface to assume an operable condition for application to the subject.

2. The automatic external defibrillator according to claim 1 wherein the at least one electrode support surface is an outer surface of the defibrillator housing.

3. The automatic external defibrillator according to claim 2 wherein the at least one electrode support surface includes a coating dimensioned and adapted to facilitate release of each electrode pad from the at least one electrode support surface to assume the operable condition.

4. The automatic external defibrillator according to claim 1 including a carrier member mounted to the defibrillator housing, the carrier member having opposed sides defining opposed electrode support surfaces, the electrode pads being mounted to respective opposed sides of the carrier member.

5. The automatic external defibrillator according to claim 4 wherein the carrier member is mounted to the defibrillator housing via a hinge.

6. The automatic external defibrillator according to claim 5 wherein the electrode pads each include a pull tab to facilitate removal of the electrode pads from the respective opposed sides of the carrier member.

7. An automatic external defibrillator, which comprises:
- a defibrillator housing including circuitry adapted to deliver electrical signals to a heart of a subject during a cardiac emergency and having an electrical connector;
- a pair of defibrillation electrode pads pre-connected to the electrical connector of the housing, the electrode pads each having a conductive hydrogel layer; and
- a pair of spaced apart brackets extending from the housing, the brackets configured and dimensioned to operatively engage the electrode pads to retain the electrode pads in fixed relation to the housing when in a stored condition thereof and permitting release of the electrode pads to an operable condition for application to the subject.

8. The automatic external defibrillator according to claim 7 wherein the electrode pads have a release liner adhered to the hydrogel layer to minimize moisture loss when in the stored condition, the release liner sized to extend across a space defined by the pair of brackets, the brackets being configured to retain the release liner in close proximity to the housing.

9. An automatic external defibrillator, which comprises:
- a defibrillator housing including circuitry adapted to deliver electrical signals to a heart of a subject during a cardiac emergency;
- a pair of defibrillation electrode pads in electrical communication with the circuitry of the defibrillator housing, the electrode pads each having a conductive hydrogel layer, and at least one release liner releasably adhered to the conductive hydrogel layer to minimize moisture loss of the hydrogel layer; and
- a two-part fastener mechanism selectively securing each of the pair of defibrillation electrode pads to the housing, at least one first member of the two-part fastener mechanism being secured to the housing and at least one second member of the two-part fastener mechanism being secured to the electrode pads.

10. The automatic external defibrillator according to claim 9 wherein the electrode pads include at least one backing member, the at least one backing member having the at least one second member of the two-part fastener mechanism mounted thereto.

11. The automatic external defibrillator according to claim 10 wherein the two-part fastener mechanism includes a hook and loop fastener system.

12. An automatic external defibrillator configured to deliver electrical pulses and/or shocks to a heart of a patient during a cardiac emergency, the defibrillator comprising:
- a housing including circuitry having a battery adapted to deliver electrical signals to a heart of a subject during a cardiac emergency;
- a pair of contact pads disposed on a surface of the housing; and
- a pair of defibrillation electrode pads in electrical communication with the circuitry, each electrode pad releasably mounted to a respective contact pad when in a stored condition thereof, the circuitry being automatically activated by a separation of at least one of the pair of defibrillation electrode pads from the respective contact pad.

* * * * *